(12) United States Patent
Renders

(10) Patent No.: US 10,932,934 B2  
(45) Date of Patent: Mar. 2, 2021

(54) DEVICE SUITABLE FOR INFLUENCING THE INTAKE OF FOOD THROUGH THE ORAL CAVITY OF A HUMAN

(71) Applicant: Johannes Bonefatio Thomas Maria Renders, Abcoude (NL)

(72) Inventor: Johannes Bonefatio Thomas Maria Renders, Abcoude (NL)

(*) Notice: Subject to any disclaimer, the term of this patent is extended or adjusted under 35 U.S.C. 154(b) by 271 days.

(21) Appl. No.: 15/775,402

(22) PCT Filed: Nov. 2, 2016

(86) PCT No.: PCT/NL2016/050759  
§ 371 (c)(1),  
(2) Date: May 11, 2018

(87) PCT Pub. No.: WO2017/082722  
PCT Pub. Date: May 18, 2017

(65) Prior Publication Data  
US 2020/0188152 A1   Jun. 18, 2020

(30) Foreign Application Priority Data

Nov. 12, 2015 (NL) .................................. NL2015779

(51) Int. Cl.  
*A61F 5/00* (2006.01)
(52) U.S. Cl.  
CPC .................... *A61F 5/0006* (2013.01)
(58) Field of Classification Search  
CPC .. A61F 5/0006; A61F 5/00; A61F 5/56; A61F 5/57; A61F 5/58; A61B 17/24; A61B 5/00; A61C 7/00; A61C 7/36  
See application file for complete search history.

(56) References Cited

U.S. PATENT DOCUMENTS 5,645,423 A * 7/1997 Collins, Jr. .............. A61C 7/36  
433/18  
6,138,679 A * 10/2000 Renders ................ A61F 5/0006  
128/897

(Continued)

FOREIGN PATENT DOCUMENTS

WO         97/42916 A1    11/1997

OTHER PUBLICATIONS

International Search Report carried out by the European Patent Office for PCT/NL2016/050759 dated Feb. 10, 2017.

*Primary Examiner* — Alireza Nia  
*Assistant Examiner* — Kevin S Albers  
(74) *Attorney, Agent, or Firm* — Shumaker, Loop & Kendrick, LLP

(57) ABSTRACT

The invention relates to a device suitable for influencing the intake of food through the oral cavity of a human, comprising anchoring means which can be applied to one or several teeth of both the upper and the lower jaw, at least one elongated element that can be placed around the front of the upper or lower jaw and that can be coupled adjacent its two element ends to the anchoring means applied to the respective jaw, and connecting means that can be provided between the upper and the lower jaw and that can be coupled at one end to the elongated element and at the other end to the anchoring means applied to the other jaw, such that an opening of the jaws causes the connecting means to pull the elongated element against the front of the jaw, which results in an unpleasant or pain sensation.

5 Claims, 5 Drawing Sheets

(56) References Cited

U.S. PATENT DOCUMENTS

| | | |
|---|---|---|
| 6,418,933 B1 | 7/2002 | Strong |
| 9,180,034 B1 | 11/2015 | Kapil |
| 2011/0277774 A1 | 11/2011 | Conell |
| 2011/0308531 A1 | 12/2011 | Grosky |
| 2014/0283849 A1* | 9/2014 | Pecina .................... A61C 7/36 128/869 |

* cited by examiner

DEVICE SUITABLE FOR INFLUENCING THE INTAKE OF FOOD THROUGH THE ORAL CAVITY OF A HUMAN

The invention relates to a device suitable for influencing the intake of food through the oral cavity of a human, comprising anchoring means which can be applied to one or several teeth of both the upper and the lower jaw, at least one elongated element that can be placed around the front of the upper or lower jaw and that can be coupled adjacent its two element ends to the anchoring means applied to the respective jaw, and connecting means that can be provided between the upper and the lower jaw and that can be coupled at one end to the elongated element and at the other end to the anchoring means applied to the other jaw, such that an opening of the jaws causes the connecting means to pull the elongated element against the front of the jaw, which results in an unpleasant or pain sensation.

A device as described above is known from International patent application WO 97/42916A1.

Especially in the modern age, where slimness is regarded as an ideal, overweight is a major problem for many people. Overweight is also a problem in regard to health.

A large number of therapies is known for reducing overweight and promoting weight loss. Many of these are based on the following or certain diets wherein it is attempted either to limit the quantities of food consumed or to regulate the intake such that certain nutrients are avoided. Other known therapies are based on the use of pharmaceutical substances that act on the digestive system.

These known therapies have the disadvantage that for many people diets are often difficult to follow or to keep up. Furthermore, pharmaceutical means often introduce undesirable substances into the human body, which may have less desirable side effects.

On the assumption that overweight is mainly caused by the intake of too much food, it is also known in the case of bulimia patients to fix the jaws, after which it will only be possible to provide food in a very special manner and in liquid form. Such a method is obviously not suitable for normal people who wish to reduce weight (permanently) or want to limit their weight, because this will not yield positive effects in the long term.

The present invention is also based on the assumption that it is advisable to influence the quantity of food taken in through the oral cavity in order to reduce overweight and thus has for its object to provide means by which the intake of food can be hampered, in fact in a measured manner.

The device described in the cited WO 97/42916A1, however, is built up from several separate components, such as a spring that counteracts a movement of the elongated element while at the same time generating a limited sensation of unpleasantness or pain. This results in a body reflex whereby a further opening of the mouth is counteracted and the person is conditioned for the future so as to modify the opening of his/her mouth, i.e. not to beyond the pain limit. In addition, the known device is fixedly and permanently adjusted for the relevant person and cannot be modified without major manipulations inside the mouth.

To achieve the set objective, the device according to the invention is characterized in that the connecting means are composed of a wire-shaped element that is rigid in longitudinal direction and that is connected at its one end to the anchoring means applied to the other jaw and at its other end is coupled to the free element end of the elongated element.

The construction of the connecting means as a wire-shaped element that is rigid in longitudinal direction and that is connected at its one end to the anchoring means applied to the other jaw and at its other end is coupled to the free element end of the elongated element provides a more direct connection between the two jaws, wherein the movement of the jaws away from each other can be accurately adjusted on the basis of the physiological build of the mouth as well as on the desired food intake therapy that is to be followed.

In an embodiment, more specifically, the free element end of the elongated element is provided with an opening through which the longitudinally rigid wire-shaped element can be passed, while the free end of the longitudinally rigid wire-shaped element is provided with a thickened portion. A loose, interlocking coupling is realized in this manner which allows some free, but limited movement between the jaws and at the same time sets a maximum for the opening of the mouth.

More specifically, the coupling between the elongated element and the anchoring means applied to the jaw is a hinged coupling. This coupling is simple and reliable and does not damage the vulnerable tissue inside the mouth.

It is also possible in a specific embodiment that the associated anchoring means are provided with a pin facing away from the tooth, which pin can be accommodated in a hinge opening provided in the elongated element adjacent the free element end thereof. This makes for a simple placement, removal or adaptation of the elongated element in the mouth without complicated dental operations having to be carried out. A device according to the invention can in fact be provided in the oral cavity within a short period of time and without anaesthetics In a further embodiment, a freely sliding sleeve element is provided around the longitudinally rigid wire-shaped element. This sleeve element ensures that the elongated element hinged in upward direction and toward the nose will hinge or spring back when the mouth is closed again.

In a further embodiment, the portion of the elongated element to be placed around the upper or lower jaw is provided with one or several local thickened portions. These thickened portions serve as contact points with the jaw whereby an additional sensation of unpleasantness or pain can be generated.

The invention will now be explained in more detail with reference to a drawing, in which:

FIG. 1 diagrammatically shows a skull with opened jaws;

For a better understanding of the invention, corresponding components have been given the same reference numerals in the ensuing description of the different figures.

It should further be noted that the figures show only those portions of the oral cavity that are necessary for a correct understanding of the present invention.

Figure 1:
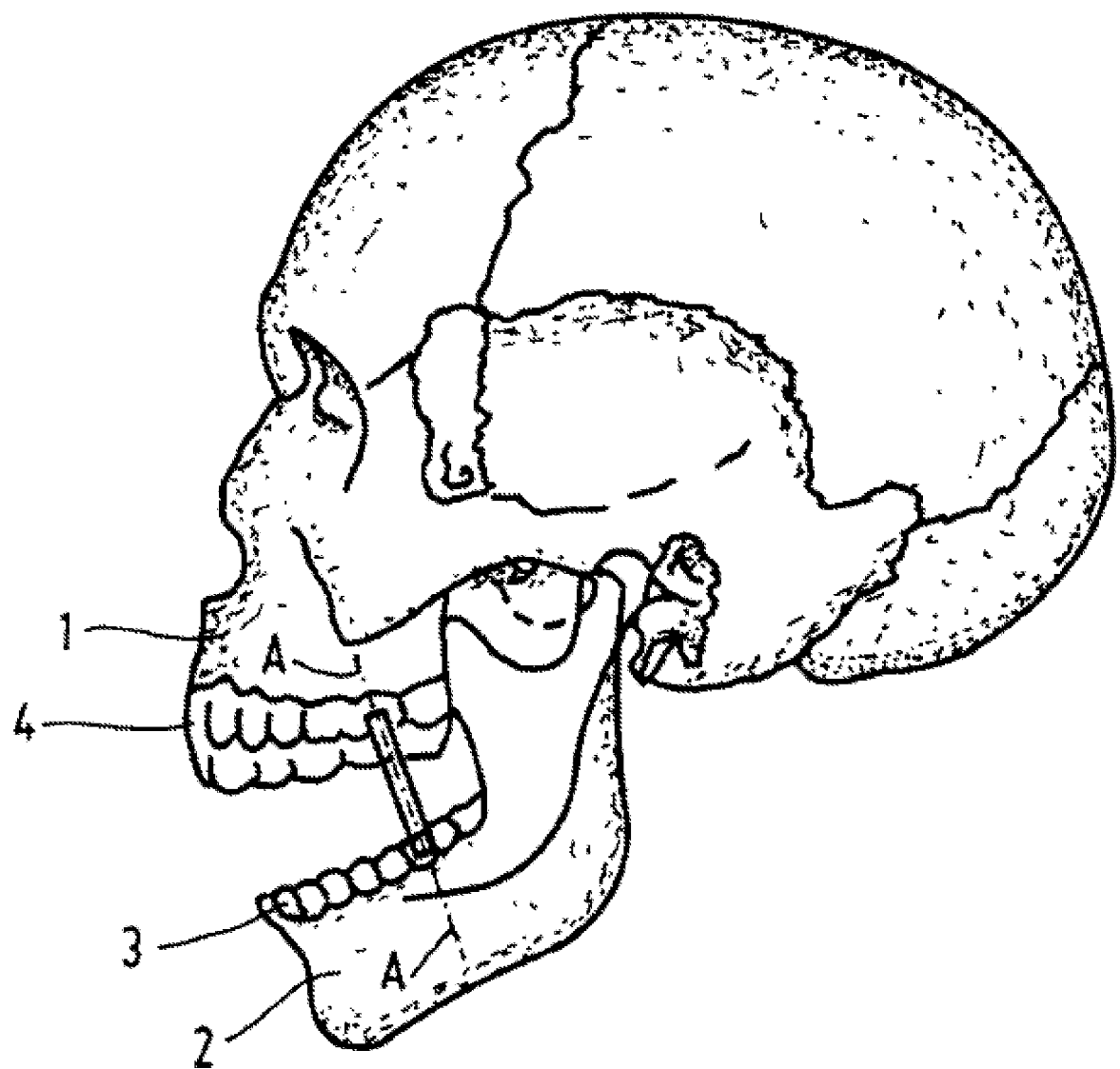
Figure 2:
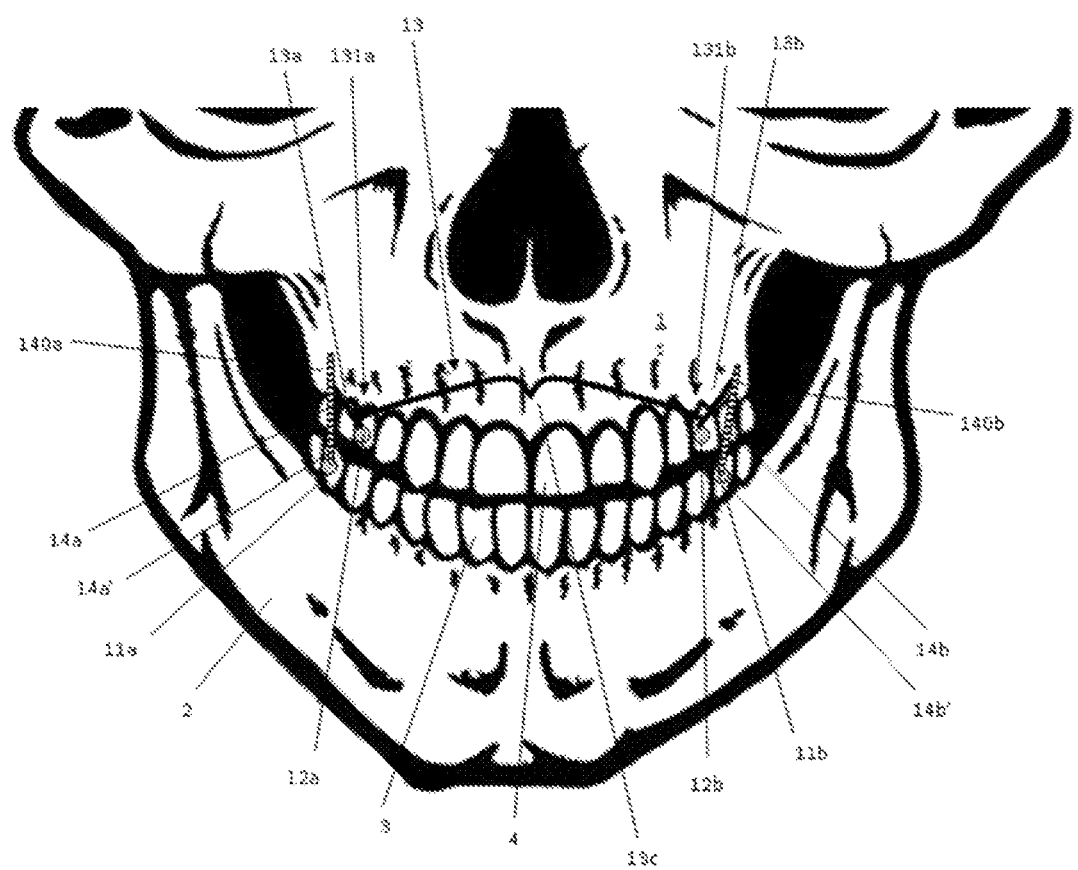
FIG. 2 is a front elevation of part of a skull provided with an embodiment of a device according to the invention.

In FIG. 1, reference numeral 1 denotes an upper jaw and reference numeral 2 a lower jaw which is in an open position relative to the upper jaw. A set of lower teeth 3 and of upper teeth 4 is accommodated in the respective lower and upper jaws in a known manner FIG. 2 shows a portion of a human skull formed by the upper jaw 1 and lower jaw 2 in front elevation. The upper set of teeth 4 is present in the upper jaw 1 and the lower set of teeth 3 is present in the lower jaw 2. The mouth is shown in the closed position. This figure also shows an embodiment of a device for influencing the intake of food through the mouth according to the invention.

Reference numerals 11a-11b and 12a-12b denote anchoring means in the form of a dental anchor which can be applied to one or several teeth 3 and 4, respectively, of both the lower jaw 2 and/or the upper jaw 1 on either side of the mouth. Such anchoring means are generally known and are widely used in orthodontic treatments for providing dentures.

Figure 3:
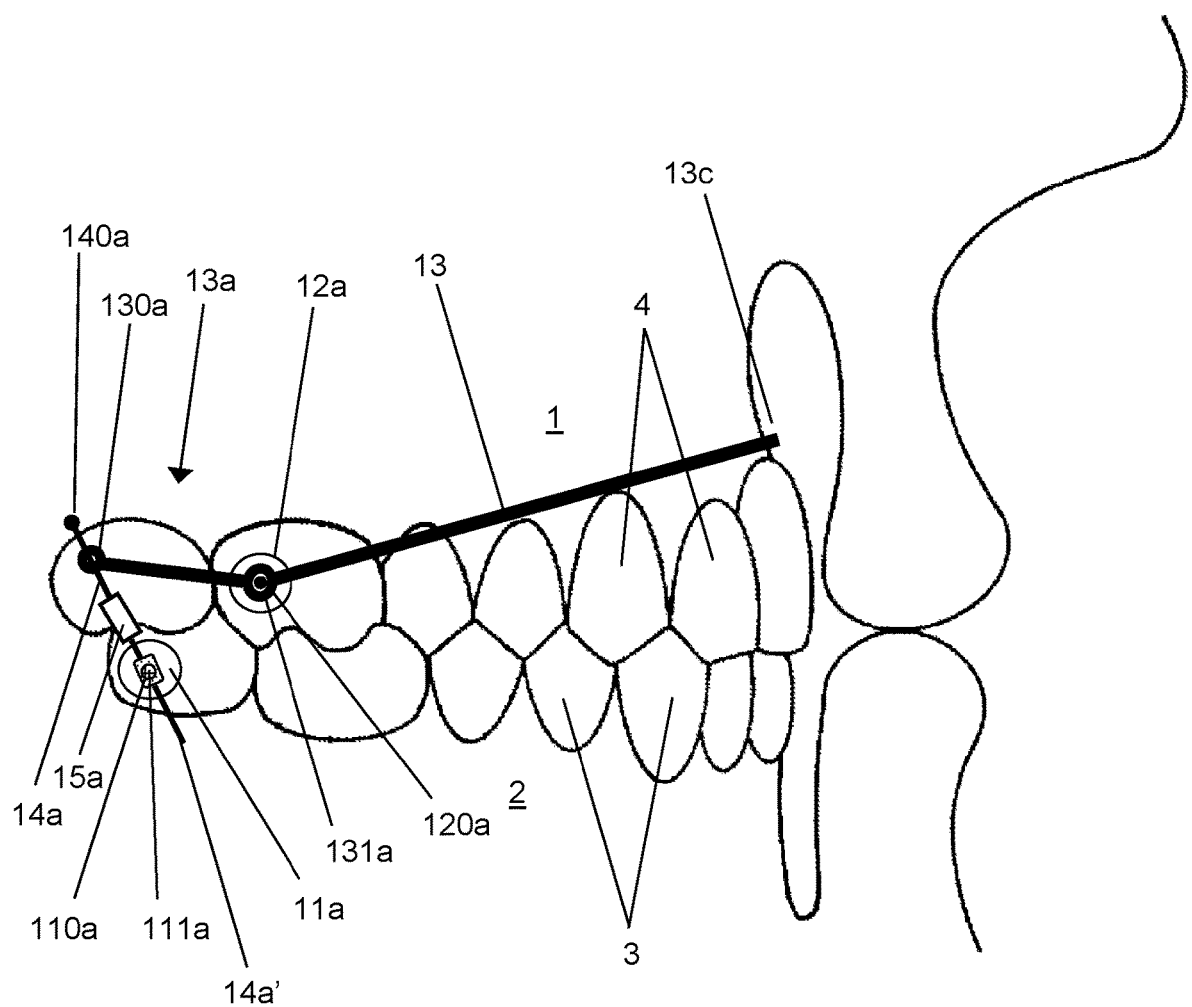
FIG. 3 is a side elevation of part of a skull provided with an embodiment of a device according to the invention, with the mouth closed.
Figure 4:
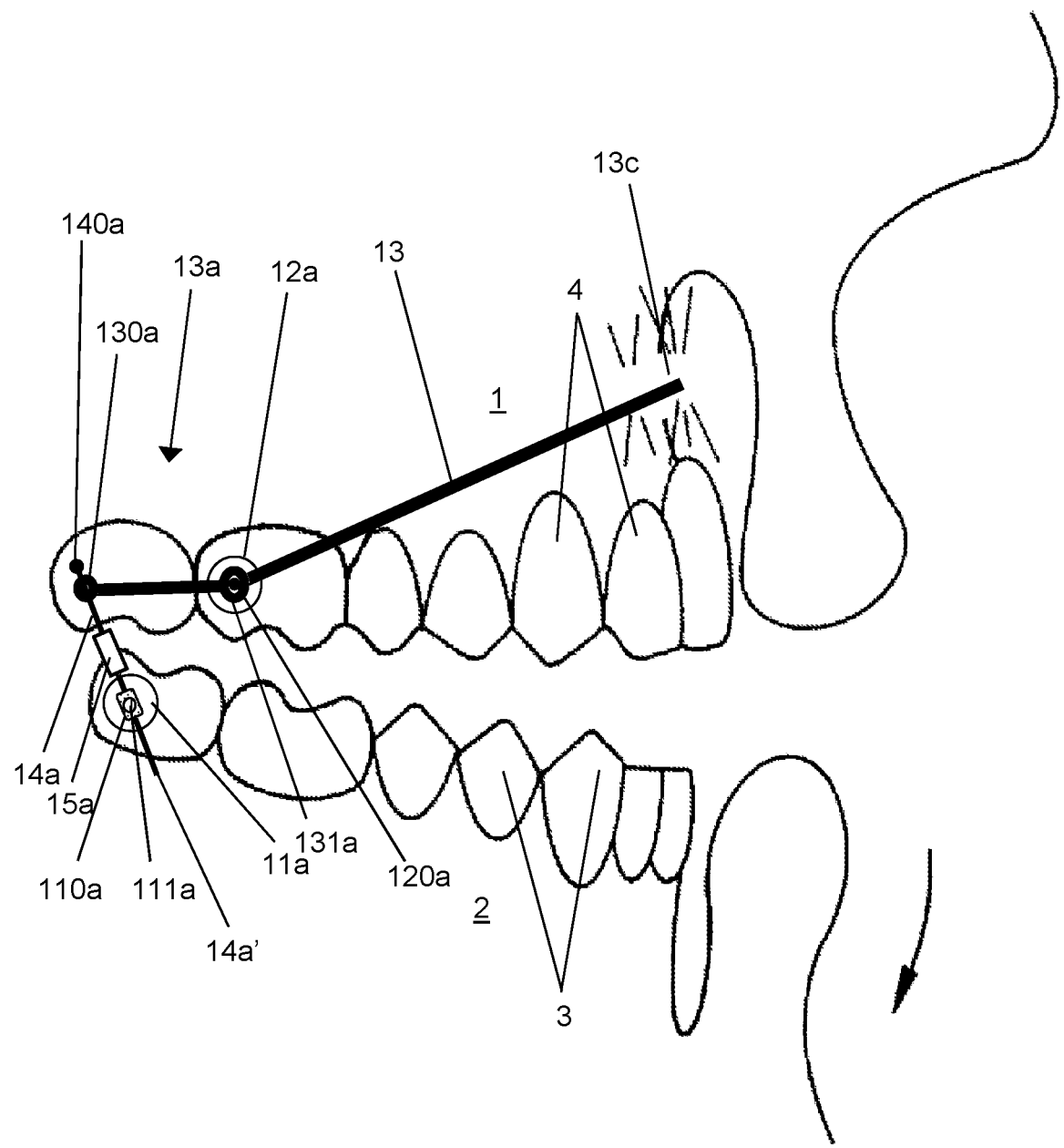
FIG. 4 is a side elevation of part of a skull provided with an embodiment of a device according to the invention, with the mouth open.

According to the invention, the device is further provided with at least an elongated element 13 that can be placed around the front of a jaw, the upper jaw 1 in this case, that follows the contour of the upper jaw as is also shown in FIGS. 3 and 4, and that is coupled adjacent the element ends 13a-13b to the anchoring means 12a-12b provided on the teeth 4 of the upper jaw 1.

Reference numerals 14a and 14b denote connecting means in the form of a connector that can be provided between the upper and the lower jaw. The connecting means 14a-14b are constructed as a wire-shaped element that is rigid in longitudinal direction and that is fixedly connected by a first end 14a'-14b' to the respective anchoring means 11a-11b and is movably coupled by its other end 140a-140b to the free element end 13a-13b of the elongated element 13 that lies around the upper jaw 1.

FIGS. 3 and 4 diagrammatically show the lower and upper sets of teeth 3 and 4 in a closed and an open position of the lower and upper jaws 2 and 1, respectively, viewed from the right-hand side of the face. An elongated wire-shaped element 13 is provided around the upper jaw here, extending from the right-hand side to the other, left-hand side (not shown) of the jaw. The wire-shaped element 13 is bent at the area of its central portion 13c so as to follow the contour of the jaw, in this embodiment the upper jaw 1. It will be obvious that the elongated wire-shaped element 13 may be bent around the lower jaw in an alternative embodiment. The function of this lower-jaw arrangement is identical to that of the embodiment as shown here in FIGS. 3 and 4 (and FIG. 2).

FIG. 3 shows the lower jaw 2 and upper jaw 1 in a closed mouth in which the teeth 3 and 4 of the lower and upper jaw, respectively, are placed on one another. The elongated element 13 is provided around the contour of the upper jaw 1, as shown, and is bent adjacent its central portion 13c (see also FIG. 2). Near the free element end 13a, the elongated element 13 is provided with an eyelet or opening 131a which is hinged to the anchoring means 12a provided on an upper tooth 4 of the upper set of teeth. The anchoring means 12a are here provided with a projecting pin 120a that can be accommodated in the opening 131a or eyelet 131a of the elongated element 13.

In an alternative embodiment, the elongated element 13 may be bent at the area of the anchoring means 12a-12b, so that the bent portion 131a (131b) of the elongated element 13 is provided around the projecting hinge pin 120a (120b).

Since the elongated element 13 is preferably made from a rigid, but bendable material, preferably a metal wire, the elongated element 13 thus shaped can be bent somewhat outwards, so that the opening or eyelet 131a and the corresponding opening or eyelet 131b at the other side of the jaw can be arranged around the respective projecting pin 120a or 120b in a simple manner. After being released the two free element ends 13a-13b will spring back so that the two openings or eyelets 131a and 131b will extend to around the respective pins 120a-120b of the anchoring means 12a-12b.

Then the placement of the opening or eyelet 131a-131b around the projecting pin 120a-120b can be secured by means of a closing cap (not shown) so that an inadvertent detachment of the elongated element 13 from around the relevant hinge pins 120a-120b can be prevented.

The free element end 13a (at the right-hand side of the mouth) and the free element end 13b (at the left-hand side of the mouth) are also each provided with a respective eyelet 130a-130b. The longitudinally rigid wire-shaped connecting element 14a (14b) is accommodated in the corresponding eyelet 130a-130b and is fixedly connected at its free end 14a' (14b') to the anchoring means 11a (11b) fastened on a tooth 3 of the lower jaw 2.

The anchoring means 11a (11b) fastened on the tooth 3 of the lower jaw 2 are provided with a hollow sleeve element 110a (110b) that is fixedly fastened on the anchoring means 11a (11b). The free end 14a' (14b') of the longitudinally rigid wire-shaped connecting element 14a (14b) is accommodated in the opening of the sleeve element 110a (110b) and clamped in said sleeve element 110a (110b) by means of a setscrew 111a (111b). A fixed assembly can be realized in this manner between the anchoring means 11a (11b) and the longitudinally rigid wire-shaped connecting element 14a (14b).

The longitudinally rigid wire-shaped connecting element 14a (14b) extends through the opening 130a (130b) on the free element end 13a (13b) of the elongated element 13 and is provided with a spherical bulge 140a (140b) at its free end, which bulge has an external dimension greater than the internal dimension of the opening 130a (130b). When the mouth is opened in that the lower jaw 2 moves down as shown in FIG. 4, the lower teeth 3 will move away from the upper teeth 4, whereby the anchoring means 11a (11b) and 12a (12b) will also move away from one another. Owing to the fixed connection between the elongated rigid connecting element 14a (14b) and the anchoring means 11a (11b) via the sleeve element 110a (110b) and the setscrew 111a (111b), the spherical bulge 140a (140b) will be checked by the opening 130a (130b) of the free element end 13a (13b). As the mouth is opened further, the free element end 13a (13b) will be carried along with the downward movement of the lower jaw by the longitudinally rigid wire-shaped connecting element 14a (14b) (in fact, by the spherical bulge 140a-140b which abuts against the opening 130a-130b), so that the elongated element 13 hinges about the pin 120a (120b) of the anchoring means 12a (12b). An identical hinging movement takes place at the left-hand side of the jaws, so that the curved elongated element 13 hinges upwards towards the nose of the person and finally presses with its central portion 13c against the upper jaw. This will result in an unpleasant or pain sensation, so that a further opening of the mouth is counteracted through a reflex action.

In an alternative functional embodiment, the longitudinally rigid connecting element 14a (14b) is provided with a loop (not shown) provided through and around the opening 130a (130b) such that it blocks any excessive opening of the mouth in a similar manner.

Although this is not shown, the central portion 13c may be provided with thickened portions which provide additional contact points with the jaw, said contact points creating an additional sensation of unpleasantness or pain.

Furthermore, a tubular element 15a (15b) is provided around the longitudinally rigid wire-shaped connecting element 14a (14b) so as to press against the eyelet 130a (130b) of the free element end 13a (13b) when the mouth is closed again, thus achieving a return movement about the hinge pin 120a (120b). This prevents the curved elongated element 13 from remaining in its hinged-up position shown in FIG. 4 when the mouth is closed again (for example, through being partly closed in or clamped by the upper lip).

The longitudinally rigid, wire-shaped connecting element 14a (14b) is preferably made from a synthetic resin, but a (twisted) metal wire is also possible.

Figure 5:
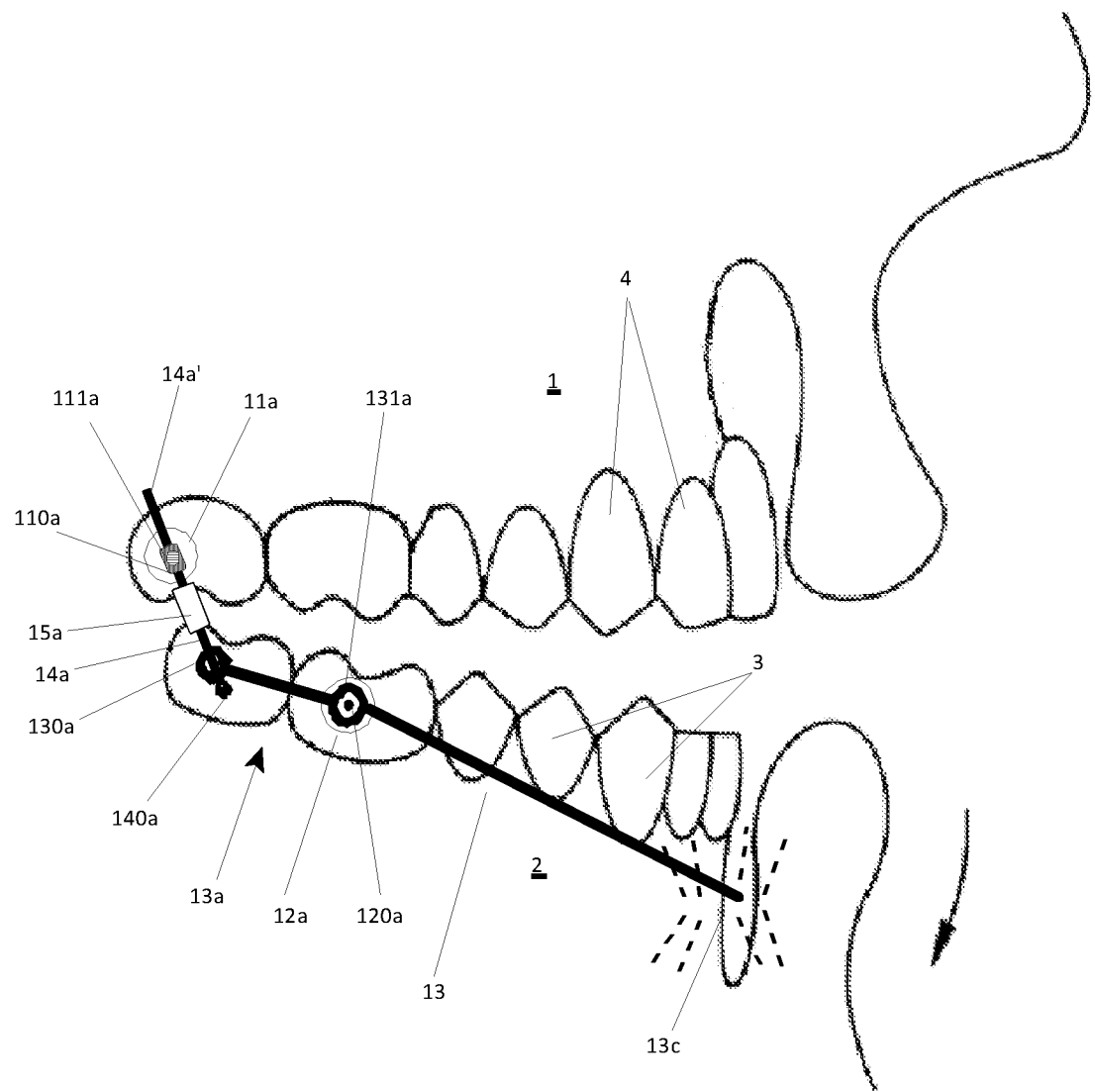
FIG. 5 is a side elevation of part of a skull provided in an embodiment of a device according to the invention, with the mouth open.

As shown in FIG. 5, the device can be attached to the lower jaw 2.

It will be clear from the above that the invention provides a method and means for influencing the intake of the food quantity by a human by reducing the intake capacity of the mouth. Overweight can be counteracted thereby and a reduction of any overweight that may be present can be achieved. It was found that the results of this method are noticeable after a very short period already, and it was empirically found that, once achieved, the target weight is maintained wholly or at least partly. After the desired weight has been achieved, the means for carrying out the method according to the invention may be removed from the oral cavity, upon which it was found that the user of these means continues to profit from the applied method for a longer period. Should the weight increase again after some time, the means can be placed in the oral cavity again.

It will be apparent from the above that the invention provides a method and means for counteracting overweight, wherein the user can continue to eat, albeit in a slower tempo than before, so that the method causes no or only a small reduction in the eating pleasure of the user.

Although the FIGS. 3, 4 and 5 show only one half of the oral cavity (the right-hand side), it will be obvious that the means in question are also present at the other side of the mouth.

The invention claimed is:

1. A device suitable for influencing the intake of food through the oral cavity of a human, comprising:
    (a) a plurality of dental anchors adapted to be applied to one or several teeth of both the upper and the lower jaw;
    (b) at least one elongate element having free first and second element ends adapted to be placed around the front of the upper or lower jaw and coupled adjacent its free first and second element ends to respective first and second dental anchors applied to the respective jaw, wherein the coupling between the elongated element and at least one of the first or second dental anchors is a hinged coupling;
    (c) a connector provided for placement between the upper and the lower jaw and having a first end and a second end, and adapted to be coupled by the second end to the free element end of the elongate element and by the first end to a third dental anchor on an opposite respective jaw of the first and second dental anchors such that an opening of the upper and lower jaws causes the connector to hinge the elongate element around the hinged coupling and against the front of the jaws, resulting in a pain sensation; and
    (d) wherein the connector comprises a wire-shaped element that is rigid in a longitudinal direction and includes a coupling by which the connector is movably coupled to the second end of the elongate element and is provided with an opening through which the longitudinally rigid wire-shaped element is adapted to be passed, further wherein the connector is provided with a thickened portion.

2. A device according to claim 1, characterized in that at least one of the plurality of dental anchors is provided with a pin facing away from at least one of the teeth, which pin is adapted to be accommodated in a hinge opening provided in the elongate element adjacent a free end thereof.

3. A device according to claim 1, wherein a freely sliding sleeve element is provided around the longitudinally rigid wire-shaped element of the connector.

4. A device according to claim 1, wherein a portion of the elongate element to be placed around the upper or lower jaw is provided with one or several local thickened portions.

5. A device suitable for influencing the intake of food through the oral cavity of a human, comprising:
    (a) a plurality of dental anchors adapted to be applied to one or several teeth of both the upper and the lower jaw and including a pin facing away from at least one of the teeth, which pin is adapted to be accommodated in a hinged opening provided in an elongate element adjacent a free end thereof;
    (b) the elongate element having first and second element ends adapted to be placed around the front of the upper or lower jaw and coupled adjacent its first and second element ends to a respective first and second dental anchors applied to the respective jaw; and
    (c) a connector provided for placement between the upper and the lower jaw and having a first end and a second end, and adapted to be coupled by the second end to the elongate element and by the first end to a third dental anchor on an opposite respective jaw of the first and second dental anchors such that an opening of the upper and lower jaws causes the connector to pull the elongate element against the front of the jaws, resulting in a pain sensation; and
    (d) wherein the connector comprises a wire-shaped element that is rigid in a longitudinal direction and includes a freely sliding sleeve element positioned around the longitudinally rigid wire-shaped element of the connector, a hinged coupling by which the connector is movably coupled to the second end of the elongate element and an opening through which the longitudinally rigid wire-shaped element is adapted to be passed.

* * * * *